US00PP14659P29

(12) United States Plant Patent

Mena et al.

(10) Patent No.: US PP14,659 P2

(45) Date of Patent: Mar. 30, 2004

(54) DOUBLE IMPATIENS PLANT NAMED 'BALOLEPEP'

(50) Latin Name: *Impatiens walleriana*
Varietal Denomination: Balolepep

(75) Inventors: Carlos Mena, Cartago (CR); Germán Tencio, Cartago (CR)

(73) Assignee: Ball Horticultural Co., West Chicago, IL (US)

( * ) Notice: Subject to any disclaimer, the term of this patent is extended or adjusted under 35 U.S.C. 154(b) by 0 days.

(21) Appl. No.: 10/385,240

(22) Filed: Mar. 10, 2003

(51) Int. Cl.[7] ..... A01H 5/00

(52) U.S. Cl. ..... Plt./317

(58) Field of Search ..... Plt./317, 319

(56) References Cited

U.S. PATENT DOCUMENTS

PP8,340 P * 8/1993 Verhoeven ..... Plt./317
PP9,276 P * 9/1995 Cole ..... Plt./317
PP9,603 P * 7/1996 Leue ..... Plt./317

OTHER PUBLICATIONS

UPOV ROM GTITM Computer Database, GTI Jouve Retrieval Software 2003/04 Citation for 'Balolepep'.*

* cited by examiner

*Primary Examiner*—Bruce R. Campell
*Assistant Examiner*—W C Haas
(74) *Attorney, Agent, or Firm*—C. A. Whealy

(57) ABSTRACT

A new and distinct cultivar of Double Impatiens plant named 'Balolepep', characterized by its compact, upright, outwardly spreading and mounded plant habit; freely branching growth habit; green and pale yellow variegated leaves; and red purple and light pink bi-colored flowers that are fully double and positioned above the foliage.

2 Drawing Sheets

Botanical classification/cultivar designation: *Impatiens walleriana* cultivar Balolepep.

BACKGROUND OF THE INVENTION

The present Invention relates to a new and distinct cultivar of Double Impatiens plant, botanically known as *Impatiens walleriana*, and hereinafter referred to by the name 'Balolepep'.

The new Double Impatiens is a naturally-occurring branch sport mutation of the *Impatiens walleriana* cultivar Sparkler Rose, disclosed in U.S. Plant Pat. No. 9,603. The new Impatiens was discovered and selected by the Inventors in October, 1999, within a population of plants of the cultivar Sparkler Rose in a controlled environment in Cartago, Costa Rica.

Asexual reproduction of the new cultivar by terminal cuttings taken at Cartago, Costa Rica since October, 1999, has shown that the unique features of this new Impatiens are stable and reproduced true to type in successive generations of asexual reproduction.

SUMMARY OF THE INVENTION

The following traits have been repeatedly observed and are determined to be the unique characteristics of 'Balolepep'. These characteristics in combination distinguish 'Balolepep' as a new and distinct Double Impatiens cultivar:

1. Compact, upright, outwardly spreading and mounded plant habit.
2. Freely branching growth habit.
3. Green and pale yellow variegated leaves.
4. Red purple and light pink bi-colored flowers that are fully double and positioned above and beyond the foliage.

Plants of the new Impatiens are most similar to plants of the parent, the cultivar Sparkler Rose. In side-by-side comparisons conducted in West Chicago, Ill., plants of the new Impatiens differed from plants of the cultivar Sparkler Rose in the following characteristics:

1. Plants of the new Impatiens were more compact and smaller than plants of the cultivar Sparkler Rose.
2. Plants of the new Impatiens had shorter internodes than plants of the cultivar Sparkler Rose.
3. Plants of the new Impatiens and the cultivar Sparkler Rose differed in flower color.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new Impatiens.

The photograph on the first sheet comprises a side perspective view of a flowering plant of 'Balolepep'.

The photograph on the second sheet is close-up view of a typical flower and leaves of 'Balolepep'.

DETAILED BOTANICAL DESCRIPTION

The cultivar Balolepep has not been observed under all possible environmental conditions. The phenotype may vary somewhat with variations in environment such as temperature and light intensity without, however, any variance in genotype. The aforementioned photographs and following observations and measurements describe plants grown in West Chicago, Ill., under commercial practice in a polycarbonate-covered greenhouse with day temperatures ranging from 18 to 24° C., night temperatures ranging from 10 to 17° C. and light levels ranging from 4,000 to 6,000 footcandles. Rooted young plants were planted in 10-cm containers and had been growing for about eight weeks when the photographs and the description were taken.

In the following description, color references are made to The Royal Horticultural Society Colour Chart, 2001 Edition, except where general terms of ordinary dictionary significance are used.

Botanical classification: *Impatiens walleriana* cultivar Balolepep.

Parentage: Naturally-occurring branch sport mutation of *Impatiens walleriana* cultivar Sparkler Rose, disclosed in U.S. Plant Pat. No. 9,603.

Propagation:

*Type cutting.*—Terminal cuttings.

*Time to initiate roots.*—About 7 days at 18° C.

*Time to produce a rooted young plant.*—About 21 days at 18° C.

*Root description.*—Fibrous.

*Rooting habit.*—Freely branching.

Plant description:

*General appearance.*—Compact, upright, outwardly spreading and mounded plant habit.

*Growth and branching habit.*—Moderately vigorous and freely-branching growth habit with about three or four basal branches; lateral branches potentially forming at every node; dense and bushy growth. Pinching, that is, removal of the terminal apices, is not required, but enhances branching.

*Plant height.*—About 13.4 cm.

*Plant diameter or spread.*—About 29.8 cm.

*Lateral branches.*—Length: About 10.2 cm. Diameter: About 6 mm. Internode length: About 2.2 cm. Texture: Smooth, glabrous. Color: 146A with random streaks and spots of 183A.

*Foliage description.*—Arrangement: Alternate, simple. Length: About 4.4 cm. Width: About 2.7 cm. Shape: Ovate. Apex: Acuminate. Base: Attenuate. Margin: Crenate with ciliation. Texture, upper and lower surfaces: Smooth, glabrous. Venation pattern: Pinnate. Color: Developing foliage, upper surface: 137A; towards the margin, 4B. Fully expanded foliage, upper surface: 137A; towards the margin, 4D. Developing and fully expanded foliage, lower surface: Lighter than 137D; towards the margin, 4D. Venation, upper and lower surfaces: 144A. Petiole: Length: About 2.4 cm. Diameter: About 2 mm. Texture, upper and lower surfaces: Smooth, glabrous. Color: 144B.

Flower description:

*Flower type and habit.*—Numerous and consistently double flowers. Flower buds open similar to a rose in fullness; flowers rounded in shape. Flowers arise from leaf axils. Freely flowering, usually about three to four flowers per lateral branch. Flowers positioned above the foliage and typically face upright, outward or downward. Flowers last about five to seven days under greenhouse conditions. Flowers not persistent. Flowers not fragrant.

*Natural flowering season.*—Flowering is continuous through the spring and summer in West Chicago, Ill.

*Flower size.*—Diameter: About 4 cm. Depth: About 2.2 cm.

*Flower buds* (*at stage of showing color*).—Length: About 1.2 cm. Diameter: About 1 cm. Shape: Ovoid. Color: 73C.

*Petals.*—Quantity/arrangement: About 28 per flower; imbricate. Length, outermost petals: About 2 cm. Width, outermost petals: About 1.3 cm. Length, innermost petals: About 1 cm. Width, innermost petals: About 8 mm. Shape: Obovate. Apex: Emarginate. Base: Attenuate. Margin: Entire. Texture, upper and lower surfaces: Smooth; glabrous. Color: When opening and fully opened, upper surface: Closest to 74B with random blotches of 65D; color becoming closer to darker than 74B with development. When opening and fully opened, lower surface: 73B with random blotches of 65D.

*Sepals.*—Quantity/arrangement: Five in a single whorl; one modified into an elongated spur. Calyx length: About 1 cm. Calyx diameter: About 1 cm. Shape: Elliptic. Apex: Acute. Margin: Entire. Texture, upper and lower surfaces: Smooth, glabrous. Color, upper and lower surfaces: Close to 144A. Spur length: About 2.8 cm. Spur diameter: At the flower, about 1 mm; at apex, less than 1 mm. Spur color: 36D.

*Peduncles.*—Length: About 1.7 cm. Diameter: About 1 mm. Angle: Acute. Strength: Strong. Texture: Smooth; glabrous. Color: 144C.

*Reproductive organs.*—None observed.

*Seed/fruit.*—None observed.

Disease/pest resistance: Plants of the new Impatiens have not been observed to be resistant to pathogens and pests common to Impatiens.

It is claimed:

1. A new and distinct cultivar of Double Impatiens plant named 'Balolepep', as illustrated and described.

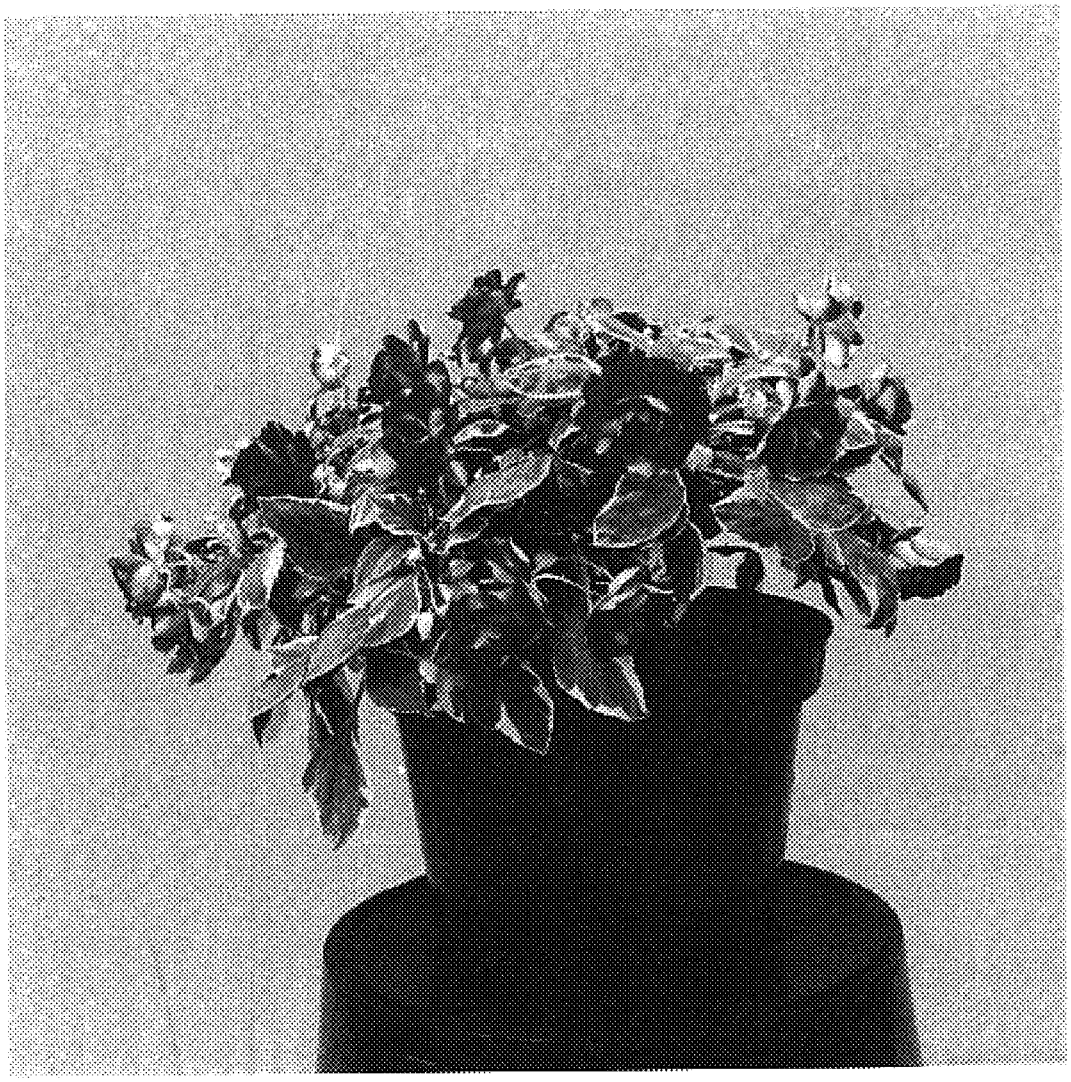

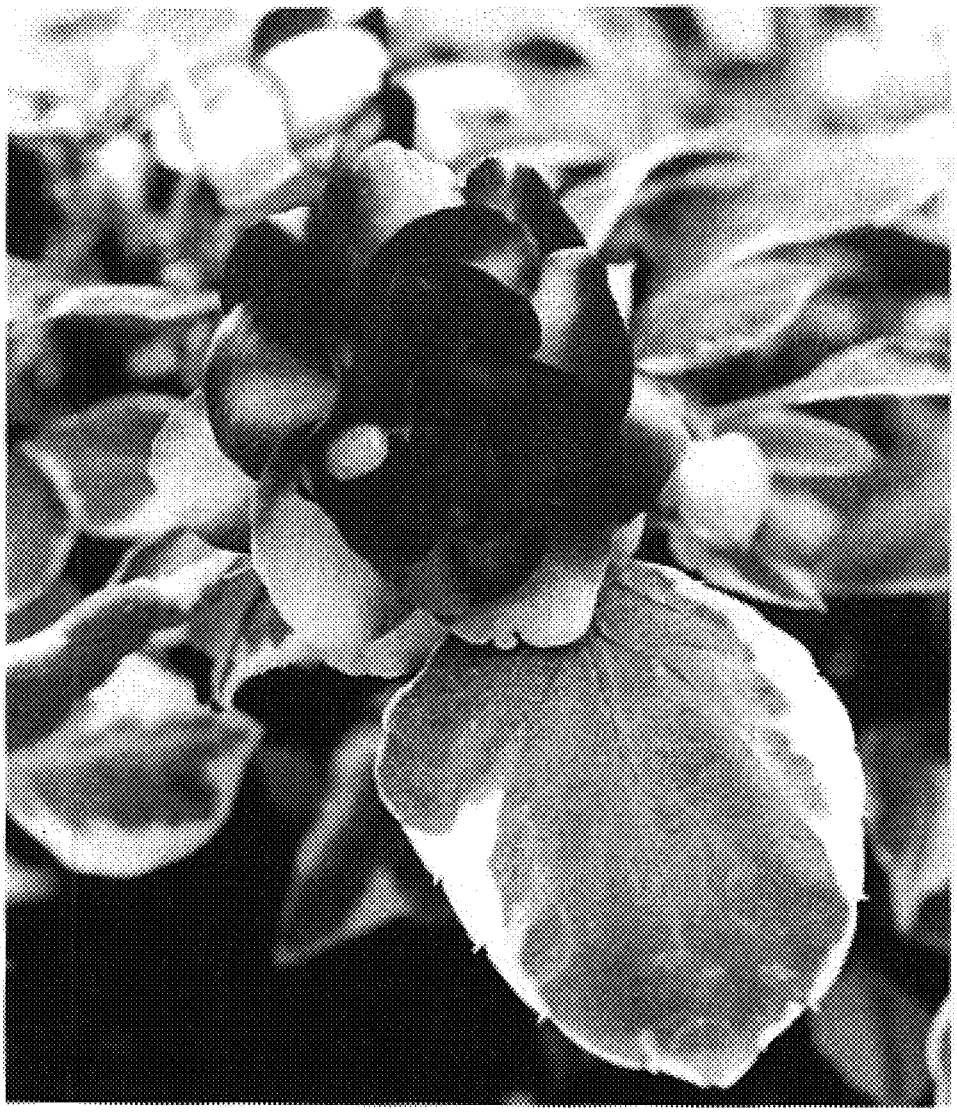

* * * * *